United States Patent [19]
Skoog et al.

[11] 3,988,338
[45] Oct. 26, 1976

[54] 4-SUBSTITUTED AMINO-2-SUBSTITUTED THIO-PYRROLO-[2,3-D]PYRIMIDINE DERIVATIVES

[75] Inventors: Folke Skoog, Madison; Ruth Y. Schmitz, Middleton, both of Wis.; Sidney M. Hecht; Robert B. Frye, both of Cambridge, Mass.

[73] Assignee: Wisconsin Alumni Research Foundation, Madison, Wis.

[22] Filed: Apr. 24, 1974

[21] Appl. No.: 463,739

[52] U.S. Cl. .............................. 260/256.5 R; 71/92; 260/256.4 F
[51] Int. Cl.² ..................................... C07D 487/04
[58] Field of Search ............................ 260/256.5 R

[56] References Cited
UNITED STATES PATENTS

| 3,037,980 | 6/1962 | Hitchings et al. | 260/256.5 R |
| 3,474,098 | 10/1969 | Hitchings et al. | 260/256.5 R |
| 3,600,389 | 8/1971 | Druey et al. | 260/256.5 R |
| 3,631,036 | 12/1971 | Kim et al. | 260/256.5 R |

Primary Examiner—Nicholas S. Rizzo
Assistant Examiner—James H. Turnipseed
Attorney, Agent, or Firm—McDougall, Hersh & Scott

[57] ABSTRACT

A series of compounds having anticytokinin activity comprising 7-amino-substituted-2-alkylthio or alkoxypyrrolo [2,3-d]pyrimidine derivatives in which the alkyl group has from 1 to 10 and preferably 4 to 7 carbon atoms and which may be substituted with halogen or hydroxyl groups.

10 Claims, No Drawings

4-SUBSTITUTED AMINO-2-SUBSTITUTED THIO-PYRROLO-[2,3-D]PYRIMIDINE DERIVATIVES

The Government has rights in this invention pursuant to Grant Nos. NSF GB-25812 and NSF GM-35269X-X₁ amended to BMS 72-02226 awarded by the National Science Foundation.

This invention relates to a group of compounds having anticytokinin activity and to the method for regulating seed development and plant growth in experimental studies and commercial applications therewith.

The term "cytokinin" has been adopted universally as a generic name for chemical substances that promote cell division and exert other growth regulatory functions in the same or similar manner as kinetin described in U.S. Pat. No. 2,903,455. Cytokinins are believed to play an important role in all phases of plant development, from cell division and enlargement to the formation of flowers and fruits. They are known to affect metabolism including the activity of enzymes and the biosynthesis of growth factors. They influence the appearance of organelles and the flow of assimilates and nutrients through the plant. They enhance its resistance to aging and to adverse environments. In general, they can be used to regulate cell division in plants, as represented by the use of kinetin for growth of excised tissues in vitro and to control plant development as represented by the use of kinetin with auxins, such as indoleacetic acid, in different proportions for the formation of shoots and roots from undifferentiated parenchyma tissue, both as described in the aforementioned patent.

In the article entitled "Cytokinins", Annual Review of Plant Physiology, Vol. 21, 1970, pages 359–383, authored by Skoog and Armstrong; in the article entitled "Cytokinins: Syntheses, Mass Spectra, and Biological Activity of Compounds Related to Zeatin", Proceedings of the National Academy of Science, Vol. 63, No. 1, 1969, pages 175–185, by Leonard, Hecht, Skoog and Schmitz; in the article entitled "Cytokinins Influence of Side-Chain Planarity of $N^6$-Substituted Adenines and Adenosines On Their Activity in Promoting Cell Growth", Phytochemistry, Vol. 9, 1970, pages 1907–1913, by Hecht, Leonard, Schmitz and Skoog; and in the article entitled "Cytokinins: Structure/Activity Relationships", Phytochemistry, Vol. 6, 1967, pages 1169–1192, by Skoog, Hamzi, Szweykowska et al, all of which are incorporated herein by reference, description is made of various of the more pertinent cytokinin compounds and the influence of various substituent groups on their cytokinin activity.

In general, compounds exhibiting cytokinin activity may be identified as adenine derivatives, preferably with the purine ring intact, and particularly the group of compounds which may be described as $N^6$-substituted adenine derivatives with the purine ring intact. These can generally be classified as purines having the general formula

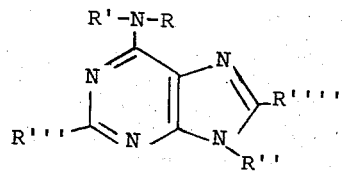

in which R' is a linear or branched alkyl or alkenyl group having between 1–10 carbon atoms with the highest activity shown by those having from 4–7 carbon atoms. R is preferably hydrogen but may also be an organic grouping of the type described for R'. Included are the hydroxy or halogen (chlorine, bromine) substituted alkyl or alkenyl groups of the type described above, aryl, alkaryl, or heterocyclic groups, as represented by phenyl, benzyl, furfuryl, thienyl, pyrimidyl, pyridyl, naphthyl, cyclopropyl and the like cycloalkyl groups, and halogenated or hydroxylated derivatives thereof. The location of the halogen or hydroxy group or the location of the unsaturated double bond in the alkyl chain or aryl ring influences the cytokinin activity of the respective derivative.

Considerable interest has been expressed in the procurement of compounds capable of functioning as cytokinin antimetabolites which are capable of use as potent cytokinin antagonists. Such antagonists can be used to extend the study of cytokinins to biological systems that do not require exogenous cytokinin. Antagonists that block the action of the endogenous cytokinin make the tissue cytokinin dependent. Such cytokinin antagonists have utility when they act in a reversible manner on the same pathway through which a cytokinin exerts its effect.

As a practical matter, such cytokinin antagonists can be employed to regulate plant development and the biosynthesis of specific products such as the tissue contents of protein, vitamins, chlorophyll and other pigments which the plant uses in its energy metabolism and in adjustment to its environment. The use of such antagonists in study or application of plant cell genetics would be appropriate means to prevent mitosis or cytokinesis while manipulating cells to cause cell fusions or differentiation. In fact, such antagonists can be used alone or in combination with cytokinins to interrupt, for short periods of time, the normal cytokinin effects on growth, etc.

In our copending application Ser. No. 285,677, filed Sept. 1, 1972, now abandoned, and entitled "Cytokinin Antagonists and Method", which application is incorporated herein by reference, description is made of a series of compounds having anticytokinin activity, and identified by the general formula:

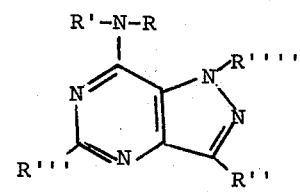

in which R and R' are as defined above; R'' is preferably methyl but may be alkyl or aryl derivatives, such as methyl, propyl, butyl, cyclopropyl, or may be the ribosyl or glucoside configuration; R' is a linear or branched chain alkyl or alkenyl group having from 1–10 carbon atoms and preferably 4–7 carbon atoms, with or without hydroxy or halogen (chlorine, bromine) substituents, such as hydroxyethylamino, n-pentyl, i-pentyl, n-butyl, i-butyl, n-hexyl, butenyl, pentenyl and the like; alicyclic groups having from 3–10 carbon atoms (substituted or unsubstituted), such as cyclopentyl, cyclohexyl; aryl, alkaryl or heterocyclic groups, substituted or unsubstituted with hydroxy or halogen groups, such as benzyl, phenyl, naphthyl, pyrimidyl, pyridyl, pyrrole and the like. Both R''' and R'''' are hydrogen but may be alkyl or other substituent.

Representative are such 7-substituted pyrazolo[4,3-d] pyrimidines as:

7-(2-hydroxyethylamino)-3-methylpyrazolo[4,3-d]pyrimidine
7-n-butylamino-3-methylpyrazolo[4,3-d]pyrimidine
3-methyl-7-(2-methylpropylamino)pyrazolo 4,3-d]pyrimidine
3-methyl-7-n-pentylaminopyrazolo[4,3-d]pyrimidine
7-cyclopentylamino-3-methylpyrazolo[4,3-d]pyrimidine
7-n-hexylamino-3-methylpyrazolo[4,3-d]pyrimidine
7-cyclohexylamino-3-methylpyrazolo[4,3-d]pyrimidine
7-n-heptylamino-3-methylpyrazolo[4,3-d]pyrimidine
7-n-decylamino-3-methylpyrazolo[4,3-d]pyrimidine
3-methyl-7-(3-methylbutylamino)pyrazolo[4,3-d]pyrimidine.

While such pyrazolo[4,3-d]pyrimidine derivatives exhibit desired anticytokinin activity, some of the compounds are limited as to the amounts that can be used, as measured by concentration since usage in excess amounts often times will have a lethal effect on the plants. Thus care must be taken in the utilization of the described cytokinin antagonists.

It is an object of this invention to provide a series of compounds which have good anticytokinin activity at low concentrations and for which there is much greater tolerance at higher concentrations with little, if any, lethal effect.

A still further object is to provide a series of anticytokinin compounds which are compatible in use with conventional cytokinin compounds to permit specific control in seed germination and plant development to maximize plant growth and output.

In accordance with the practice of this invention the improved anticytokinin effects are secured by a series of compounds which may be identified as pyrrolo[2,3-d]pyrimidine derivatives which may be represented by the following general formula:

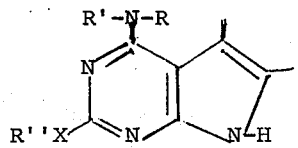

in which R and R' are linear or bridged chain alkyl or alkenyl groups having from 1–10 carbon atoms, and preferably 4–7 carbon atoms, with or without hydroxy and/or halogen (chlorine, bromine) sustituents, such as hydroxyethyl, n-pentyl, isopentyl, n-hexyl, butenyl, pentenyl and the like; cycloalkyl groups having from 3–10 carbon atoms (substituted or unsubstituted), such as cyclopentyl, cyclohexyl and the like; aryl, alkaryl, or heterocyclic groups (substituted with hydroxy or halogen groups or unsubstituted), such as benzyl, phenyl, naphthyl, pyrimidyl, pyridyl, pyrrole and the like; and in which one of the groups R or R' is preferably hydrogen; X is an atom of oxygen or sulphur, R'' is an alkyl, alkenyl, cycloalkyl, alicyclic, aryl, alkaryl or heterocyclic group of the type described for R or R', and preferably a low carbon ($C_1$ to $C_5$) (substituted or unsubstituted) alkyl or alkenyl group and more preferably methyl. The compounds of this invention may be further represented by the following general formula

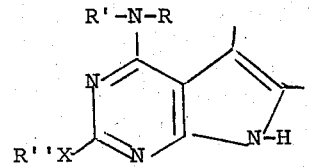

in which X is a group selected from the group consisting of -O-, -SO, -N-, and -$CH_2$-, R and R' is a group selected from the group consisting of an alkyl and an alkenyl group having from 4 to 7 carbon atoms and hydroxyl and halogen derivatives thereof, (R is usually H), R'' is selected from the group consisting of a substituted and unsubstituted group selected from the group consisting of an alkyl and alkenyl group having from 1 to 10 carbon atoms, a cycloalkyl group having from 3 to 10 carbon atoms, an aryl group, an alkaryl group and a heterocyclic group, R''' and R'''' is an organic group similar to R and R' but preferably hydrogen.

The preferred pyrrolo[2,3-d]pyrimidine derivatives comprise the 2-alkylthiopyrrolo[2,3-d]pyrimidine derivatives and more particularly the 4-substituted amino derivatives of 2-methylthiopyrrolo[2,3]pyrimidine, such as:

| | |
|---|---|
| 4-n-hexylamino-2-methylthiopyrrolo[2,3-d]pyrimidine | (1) |
| 4-n-pentylamino-2-methylthiopyrrolo[2,3-d]pyrimidine | (2) |
| 4-isopentylamino-2-methylthiopyrrolo[2,3-d]pyrimidine | (3) |
| 4-isopentenylamino-2-methylthiopyrrolo[2,3-d]pyrimidine | (4) |
| 4-cyclohexylamino-2-methylthiopyrrolo[2,3-d]pyrimidine | (5) |
| 4-cyclopentylamino-2-methylthiopyrrolo[2,3-d]pyrimidine | (6) |
| 4-n-hexylamino-2-methoxypyrrolo[2,3-d]pyrimidine | (7) |
| 4-n-pentylamino-2-methoxypyrrolo[2,3-d]pyrimidine | (8) |
| 4-isopentylamino-2-methoxypyrrolo[2,3-d]pyrimidine | (9) |
| 4-isopentenylamino-2-methoxypyrrolo[2,3-d]pyrimidine | (10) |
| 4-cyclohexylamino-2-methoxypyrrolo[2,3-d]pyrimidine | (11) |
| 4-cyclopentylamino-2-methoxypyrrolo[2,3-d]pyrimidine | (12) |

The described cytokinin antagonists of this invention correspond closely in structure and substituents to the adenine derivatives having high cytokinin activity, in which the 4-amino substituents of the pyrrolopyrimidine compounds of this invention generally correspond to the 6-substituted purine or adenine and structural similarity exists also with respect to the nuclei. Such similarity in structure is significant since it allows participation of either or both in the same type of receptor complexes.

Reversal in activity has been experienced by substitution of the alkylthiolated grouping on the corresponding position of the pyrrazolo[4,3-d]pyrimidine compounds described in the aforementioned copending application as having anti-cytokinin activity.

In the new series, the 4-substituted amino-2-methylthiopyrrolo[2,3-d]pyrimidines, activity is more selective with the result that some of the 2-methylthiolated pyrrolo[2,3-d]-pyrimidine derivatives exhibit cytokinin activity for budding, for example, while retaining their anticytokinin activity for growth. This, of course, presents a very interesting phenomenon which has widespread utilization in the study of plant growth for experimental and commercial purposes.

The following examples are given for the preparation of representative cytokinin antagonists of this invention and tests performed therein to illustrate their relative anti-cytokinin activity:

EXAMPLE 1

4-(n-hexylamino)-2-methylthiopyrrolo[2,3-d]pyrimidine:

To 200 mg of 4-chloro-2-methylthiopyrrolo[2,3-d]pyrimidine was added 2 ml of n-hexylamine. The solution was heated at reflux under nitrogen for 2 hours. The resulting dark oil was purified by chromatography on 30 g of Sephadex LH-20, elution with $H_2O$ and then with increasing concentrations of ethyl alcohol up to 40% ethyl alcohol. The appropriate fractions were combined and evaporated to dryness and the solid residue was crystallized from ethyl alcohol/water to afford white crystals of product, yield 79 mg (60%), m.p. 117.5° – 118.5°.

| EtOH $\lambda_{max}$ | (pH 1) | 297 | (13,700), | 242 | (18,700) | | | | |
|---|---|---|---|---|---|---|---|---|---|
| EtOH $\lambda_{min}$ | (pH 1) | 266 | (8,900) | | | | | | |
| EtOH $\lambda_{max}$ | (pH 7) | 286 | (15,400), | 235 | (27,200), | EtOH $\lambda_{min}$ | (pH 7) | 254 | (4,600) |
| EtOH $\lambda_{max}$ | (pH 10) | 285 | (15,800), | 233 | (28,500), | EtOH $\lambda_{min}$ | (pH 10) | 254 | (5,300) |

Found: C, 59.17; H, 7.64 - Calc. for $C_{13}H_{20}N_4S$: C, 59.06; H, 7.63%

EXAMPLE 2

2-methylthio-4-(n-pentylamino)pyrrolo[2,3-d]pyrimidine:

To 200 mg of 4-chloro-2-methylthiopyrrolo[2,3-d]pyrimidine was added 2 ml of n-pentylamine. The solution was heated at reflux under nitrogen for 2 hours. The resulting dark oil was purified by chromatography on 30 g of Sephadex LH-20, elution with $H_2O$ and then with increasing concentrations of EtOH up to 40% EtOH. The appropriate fractions were combined and evaporated to dryness and the solid residue was crystallized from EtOH/$H_2O$ to afford white crystals of product, yield 71 mg (57%), m.p. 134°–137°.

| EtOH $\lambda_{max}$ | (pH 1) | 287 | (12,400), | 238 | (20,700) | | | | |
|---|---|---|---|---|---|---|---|---|---|
| EtOH $\lambda_{min}$ | (pH 1) | 256 | (6,100) | | | | | | |
| EtOH $\lambda_{max}$ | (pH 7) | 282 | (14,000), | 234 | (24,700), | EtOH $\lambda_{min}$ | (pH 7) | 253 | (5,600) |
| EtOH $\lambda_{max}$ | (pH 10) | 283 | (12,700), | 234 | (24,400), | EtOH $\lambda_{min}$ | (pH 10) | 253 | (4,600) |

MS : m/c 250 ($M^+$), 207, 193, 180, 149
(Found: C, 57.93; H, 7.28 - Calc. for $C_{12}H_{18}N_4S$: C, 57.56; H, 7.25 %)

EXAMPLE 3

4-(3-methylbutylamino)-2-methylthiopyrrolo[2,3-d]pyrimidine:

To 100 mg of 4-chloro-2-methylthiopyrrolo[2,3-d]pyrimidine was added 2 ml of isopentylamine. The solution was heated at reflux under nitrogen for 2 hours. The resulting dark oil was purified by chromatography on 30 g of Sephadex LH-20, elution with $H_2O$ and then with increasing concentrations of EtOH up to 40% EtOH. The appropriate fractions were combined and evaporated to dryness and the solid residue was crystallized from EtOH/$H_2O$ to afford white crystals of product, yield 39 mg (38%), m.p. 157°–158° C.

| EtOH $\lambda_{max}$ | (pH 1) | 297 | (14,000), | 242 | (19,000) | | | | |
|---|---|---|---|---|---|---|---|---|---|
| EtOH $\lambda_{min}$ | (pH 1) | 268 | (8,500) | | | | | | |
| EtOH $\lambda_{max}$ | (pH 7) | 286 | (15,800), | 233 | (27,700), | EtOH $\lambda_{min}$ | (pH 7) | 254 | (4,800) |
| EtOH $\lambda_{max}$ | (pH 10) | 285 | (16,000), | 232 | (28,400), | EtOH $\lambda_{min}$ | (pH 10) | 254 | (5,000) |

(Found: C, 57.43; H, 7.32 - Calc. for $C_{12}H_{18}N_4S$ : C, 57.56; H, 7.25%

EXAMPLE 4

4-(3-methyl-2-butenylamino)-2-methylthiopyrrolo[2,3-d]-pyrimidine:

To 400 mg of 4-chloro-2-methylthiopyrrolo[2,3-d]pyrimidine was added 2 ml of isopentylamine. The solution was heated at reflux under nitrogen for 2 hours. The resulting dark oil was purified by chromatography on 30 g of Sephadex LH-20, elution with $H_2O$ and then with increasing concentrations of EtOH up to 40% EtOH. The appropriate fractions were combined and evaporated to dryness and the solid residue was crystallized from EtOH/$H_2O$ to afford white crystals of product, yield 131 mg (26%), m.p. 155.0° – 155.5°.

| | | | | | | | | | |
|---|---|---|---|---|---|---|---|---|---|
| EtOH $\lambda_{max}$ | (pH 1) | 298 | (12,900), | 243 | (17,600) | | | | |
| EtOH $\lambda_{min}$ | (pH 1) | 269 | (8,400) | | | | | | |
| EtOH $\lambda_{max}$ | (pH 7) | 286 | (14,200), | 233 | (25,800), | EtOH $\lambda_{min}$ | (pH 7) | 254 | (4,700) |
| EtOH $\lambda_{max}$ | (pH 10) | 286 | (14,800), | 234 | (25,800), | EtOH $\lambda_{min}$ | (pH 10) | 256 | (5,200) |

(Found: C, 58.29; H, 6.66 - Calc. for $C_{12}H_{16}N_4S$ : C, 58.03 H, 6.50%)

EXAMPLE 5

4-cyclohexylamino-2-methylthiopyrrolo[2,3-d]pyrimidine:

To 100 mg of 4-chloro-2-methylthiopyrrolo[2,3-d]-pyrimidine was added 2 ml of cyclohexylamine. The solution was heated at reflux under nitrogen for 2 hours. The resulting dark oil was purified by chromatography on 30 g of Sephadex LH-20, elution with $H_2O$ and then with increasing concentrations of EtOH up to 40% EtOH. The appropriate fractions were combined and evaporated to dryness and the solid residue was crystallized from EtOH/$H_2O$ to afford white crystals of product, yield 67 mg (51%), m.p. 189°–190°.

cyclohexylamino, and 4-cyclopentylamino[-2-methoxypyrrolo[2,3-d]pyrimidines are produced by substitution of 4-chloro-2-methoxypyrrolo[2,3-d]-pyrimidine for the 4-chloro-2-methylthiopyrrolo[2,3-d]pyrimidine in Examples 1 to 6.

The anticytokinin activity of the compounds prepared in Examples 1 to 6 were compared with:

| | |
|---|---|
| 7-n-pentylamino-3-methyl-5-methylthiopyrazolo-[4,3-d]pyrimidine | (13) |
| 7-isopentylamino-3-methyl-5-methylthiopyrazolo-[4,3-d]pyrimidine | (14) |
| 4-n-hexylpyrrolo[2,3-d]pyrimidine | (15) |
| 4-isopentenylpyrrolo[2,3-d]pyrimidine | (16) |

| | | | | | | | | | |
|---|---|---|---|---|---|---|---|---|---|
| EtOH $\lambda_{max}$ | (pH 1) | 294 | (12,400), | 239 | (20,600) | | | | |
| EtOH $\lambda_{min}$ | (pH 1) | 260 | (6,500) | | | | | | |
| EtOH $\lambda_{max}$ | (pH 7) | 283 | (13,200), | 234 | (25,100), | EtOH $\lambda_{min}$ | (pH 7) | 254 | (4,200) |
| EtOH $\lambda_{max}$ | (pH 10) | 284 | (13,700), | 233 | (26,000), | EtOH $\lambda_{min}$ | (pH 10) | 254 | (4,500) |

MS: m/c 262 (m+), 247, 233, 229, 219, 215, 207, 205, 193, 180, 149, 147, 134.

(Found: C, 58.05; H, 6.66 - Calc. for $C_{13}H_{18}N_4S$ . ½$H_2O$:
C, 57.54; H, 7.05. Calc. for $C_{13}H_{18}N_4S$ . ¼$H_2O$:
C, 58.51; H, 6.99 %)

EXAMPLE 6

4-(cyclopentylamino)-2-methylthiopyrrolo[2,3-d]pyrimidine:

To 100 mg of 4-chloro-2-methylthiopyrrolo[2,3-d]pyrimidine was added 2 ml of cyclopentylamine. The solution was heated at reflux under nitrogen for 2 hours. The resulting dark oil was purified by chromatography on 30 g of Sephadex LH-20, elution with $H_2O$ and then with increasing concentrations of EtOH up to 40% EtOH. The appropriate fractions were combined and evaporated to dryness and the solid residue was crystallized from EtOH/$H_2O$ to afford tan crystals of product, yield 50 mg (40%), m.p. 190°–191° C.

Comparisons of anticytokinin activity were made based upon concentrations of the respective compounds showing marked inhibition of growth in the presence of 0.003 μ 2iP [6-(3-methyl-2-butenylamino)purine,] in tobacco callus bioassay, with the following results:

TABLE I

| Compound No. | Activity | |
|---|---|---|
| | Cytokinin | Antagonist |
| | μM | μM |
| (1) | | 6 |
| (2) | | 0.24 |
| (3) | | 0.73 |
| (4) | | 0.73 |

| | | | | | | | | | |
|---|---|---|---|---|---|---|---|---|---|
| EtOH $\lambda_{max}$ | (pH 1) | 298 | (13,700), | 242 | (18,100) | | | | |
| EtOH $\lambda_{min}$ | (pH 1) | 267 | (9,800), | | | | | | |
| EtOH $\lambda_{max}$ | (pH 7) | 286 | (16,000), | 234 | (27,600) | EtOH $\lambda_{min}$ | (pH 7) | 256 | (6,300), |
| EtOH $\lambda_{max}$ | (pH 10) | 286 | (15,300), | 233 | (26,900) | EtOH $\lambda_{min}$ | (pH 10) | 256 | (5,500). |

Found: C, 57.93; H, 6.27 - Calc. for $C_{12}H_{16}N_4S$ : C, 58.05; H, 6.50%.)

EXAMPLES 7–12

The corresponding [4-n-hexylamino, 4-n-pentylamino, 4-isopentylamino, 4-isopentylamino, 4-

| | | |
|---|---|---|
| (5) | | 0.081 |
| (6) | | 0.027 |
| (13) | <2.2 | ->>6.6 |
| (14) | 0.73 | ->6.6 |
| (15) | 2.2 | ->20 |

TABLE I-continued

| Compound No. | Activity Cytokinin | Antagonist |
|---|---|---|
| (16) | μM<br>0.24 – 6.6 | μM |

From these results, it will be seen that the 4-substituted amino derivatives of 2-methylthiopyrrolo[2,3-d]-pyrimidine are active cytokinin antagonists. The 4-cyclopentylamino derivative (6) is more active than the most active of the pyrazolo[4,3-d]pyrimidines described in our aforementioned copending application. On the other hand, it will be seen that in the absence of the methylthio grouping on the 2-position of pyrrolo[2,3-d]pyrimidine, the corresponding compound showed cytokinin activity instead of anticytokinin activity. Similarly, it will be seen that the substitution of the methylthio grouping for hydrogen on the $C_5$ position of the pyrazolo-[4,3-d]pyrimidine converts the anticytokinin derivatives to compounds having cytokinin activity.

The following is a tabulation of results which show the interaction of 4-cyclopentylamino-2-methylthiopyrrolo[2,3-d]-pyrimidine (Example 6), with 2iP:

resulting suspension was treated with water and neutralized and the solid was filtered and air dried to yield 900 mg (95%) of the methylated product. This material was heated at reflux in 60 ml of $POCl_3$ and 2 ml of N,N-dimethylaniline for 2 hours. The resulting green liquid was concentrated to a syrup, poured onto crushed ice with vigorous stirring, and extracted with ether. The ether extract was dried and concentrated to afford an orange solid, yield 602 mg (61%) from the methylated intermediate. To 100 mg of this solid was added 3 ml of n-pentylamine. The resulting solution was heated at reflux for 2 hours, concentrated under diminished pressure and then purified by chromatography on a 30 g column of Sephadex LH-20, elution with water and then with an ethanol gradient to give the desired product. Recrystallization from ethanol-water afforded the product as colorless crystals, yield 90 mg (72%), mp 88°–90°;

EtOH $\lambda_{max}$ (pH 1) 317, 248, EtOH 284, 218; $\lambda_{max}$ (pH 10) 320, 238; $\lambda_{min}$ 294, 228; $\lambda_{max}$ EtOH (pH 7) 312,237, $\lambda_{min}$ 288, 231.
Mass spectrum: m/e 265 ($M^+$), 250, 236, 222, 208, 194, 179.
Anal. Calcd for $C_{12}H_{19}N_5S.\frac{3}{4} H_2O$: C, 51.69; H, 7.41.
Found: C, 51.90; H, 7.57.

EXAMPLE 14

3-methyl-7-(3-methylbutylamino)-5-methylthiopyrazolo[4,3-d]-pyrimidine:

This material was prepared as above starting with 100 mg of the chlorinated intermediate and 3 ml of isoamylamine. Recrystallization of the solid product

TABLE II

Effect of serial combinations of Compound 6 and 2iP on growth (and building) of tobacco callus.

| 2iP μM | Compound 6 (4-cyclopentylamino-2-methylthiopyrrolo[2,3-d]pyrimidine) μM | | | | | |
|---|---|---|---|---|---|---|
|  | 0 | 0.08 | 0.24 | 0.73 | 2.2 | 6.6 |
|  | FRESH WEIGHT (g/flask) | | | | | |
| 0 | 0.57 | 0.12 | 0.08 | 0.11 | 0.12 | 0.08 |
| 0.24 | 13.8 | 4.1 | 1.3 | 1.4 | 0.53 | 0.11 |
| 0.73 | 12.6 | 4.3 | 3.0 | 2.1 | 0.54 | 0.20 |
| 2.2 | 11.0 | 3.4 | 4.7 (1; 2) | 3.5 (1; 4) | 1.9 (4; 20) | 0.58 (1; 4) |
| 6.6 | 5.6 | 4.7 | 3.7 | 2.6 (1; 1) | 2.3 | 1.7 (2; 20) |
| 20.0 | 1.6 | 2.3 | 2.0 | 2.0 (2; 10) | 2.6 (7; 56) | 3.2 (9; 108) |

Growth period: May 24 to June 28, 1973 (Expt. C226)
The first number in parentheses is the number of callus per treatment which formed buds, and the second number is the total number of buds per treatment. Each treatment consisted of four flasks with a total of 12 callus pieces.

EXAMPLE 13

3-Methyl-5-methylthio-7-pentylaminopyrazolo[4,3-d]pyrimidine:

To 868 mg of 3-methyl-5-mercapto-7-hydroxypyrazolo-[4,3-d]pyrimidine (R. K. Robins, L. B. Holum and F. W. Furcht, J. Org. Chem., 21, 883 (1956) was added one equivalent of 0.1 N aqueous NaOH solution. The solution was shaken with a 10% molar excess of methyl iodinde, for 15 minutes. The from Sephadex LH-20 afforded the desired material as pale yellow crystals, yield 107 mg (85%), mp 90°–95° C;

EtOH $\lambda_{max}$ (pH 1) 316, 267 (sh), 248, EtOH $\lambda_{min}$ 285, 221; $\lambda_{max}$ (pH 10) 317, 238, $\lambda_{min}$ 294, 226; $\lambda_{max}$ EtOH (pH 7) 312,238, $\lambda_{min}$ 290, 229.
Anal Calcd for $C_{12}H_{19}N_5S.\frac{3}{4} H_2O$: C, 51.69; H, 7.41.
Found: C, 51.90; H, 7.57

EXAMPLE 15

4-(n-Hexylamino)pyrrolo[2,3-d]pyrimidine:

Into a flask equipped with a stirring bar and reflux condenser were introduced 4-(n-hexylamino)-2-methylthio-pyrrolo[2,3-d]-pyrimidine (100 mg) and 5 ml of Raney nickel ethanolic slurry (c.a. 0.6 g/ml; 10 months old). The mixture was heated at reflux and additional 5 ml portions of Raney nickel slurry were added at 12 hour intervals for 48 hours at which point tlc (24:1 CHCl$_3$-MeO) indicated that the reaction was complete. The Raney nickel was removed by filtration through Celite. Evaporation of the solvent afforded a tan solid (79 mg; 95%) which was purified by preparative tlc on silica using a solvent system of 4:1 benzene-ethanol. This purification yielded a white solid, m.p. 147°–148° C.; C$_{12}$H$_{18}$N$_4$ (M$^+$ calculated: 218.15314; found: 218.15365);

As growth inhibitors of tobacco tissue cultures, the compounds of this invention are superior to the common naturally occurring plant growth inhibitor abscisic acid (ABA) reported to be counteracted by treatment with cytokinins in the process of seed germination and various growth tests. In tests of serial combinations with 2iP, all tested concentrations of ABA (8.08 – 2.2 μM) affected the growth form of the tissue, but only the highest concentrations significantly lowered the yield of tissue. While treatments with ABA resulted in more compact tissue, they had no influence on the

| EtOH $\lambda_{max}$ | (pH 1) | 276 | (14,200), | 228 | (15,300), | EtOH $\lambda_{min}$ | (pH 1) | 240 | (2,700) |
| --- | --- | --- | --- | --- | --- | --- | --- | --- | --- |
| EtOH $\lambda_{max}$ | (pH 7) | 274 | (15,500), | EtOH $\lambda_{min}$ | (pH 7) | 240 | (2,900) | | |
| EtOH $\lambda_{max}$ | (pH 10) | 274 | (15,800), | $\lambda_{min}$ | (pH 10) | 240 | (3,600) | | |

MS: m/e 218.153, 202.133, 161.082, 147.065, 134.060, 119.049.

EXAMPLE 16

4-(3-Methyl-2-butenylamino)pyrrolo[2,3-d]pyrimidine:

To a solution of 4-(3-methyl-2-butenylamino)-2-methylthiopyrrolo[2,3-d]pyrimidine (60 mg) in ethanol (30 ml) was added 1 ml of Raney nickel ethanolic slurry (c.a. 0.6g/ml). The mixture was heated at reflux until tlc (24:1 CHCl$_3$-MeOH) indicated that the reaction was complete. The Raney nickel was removed by filtration through Celite. Evaporation of the solvent afforded a tan solid (25 mg; 51%) which was purified by preparative tlc on silica using a solvent system of 4:1 benzene-ethanol. This purification yielded an off-white solid, m.p. 202°–203° C; C$_{11}$H$_{14}$N$_4$ (M$^+$ calculated: 202.12183; found: 202.12083);

viability and caused no discoloration of the tissue.

The effect of the cytokinin antagonists of this invention in serial combinations with 2iP was also examined in callus cultures grown on medium with high cytokinin concentrations suitable for the induction of bud formation. The tests clearly indicated that the influence of the treatments on budding was roughly inversely proportional to the effect on growth.

It will be apparent from the foregoing that we have provided a new series of compounds as cytokinin antagonists and the utilization thereof in the regulation and study of plant growth.

It will be understood that changes may be made in the details of formulation and operation without departing from the spirit of the invention, especially as defined in the following claims.

| EtOH $\lambda_{max}$ | (pH 1) | 277 | (10,200), | 227 | shoulder | (11,800), | EtOH $\lambda_{min}$ | (pH 1) | | |
| --- | --- | --- | --- | --- | --- | --- | --- | --- | --- | --- |
| 248 | (4,200) | | | | | | | | | |
| EtOH $\lambda_{max}$ | (pH 7) | 274 | (10,800), | EtOH $\lambda_{min}$ | (pH 7) | 242 | (3,400) | | | |
| EtOH $\lambda_{max}$ | (pH 10) | 274 | (11,600), | EtOH $\lambda_{min}$ | (pH 10) | 242 | (4,600); | | | |

MS: m/e 202.120, 187.099, 159.066, 147.066, 134.058, 118.040

The minimum concentration for the development of the desired antagonist activity, as determined by assay, is about 0.003 μM. The maximum would be the amount which would represent a lethal dosage for the particular plant and/or antagonist, a level which can be determined by known assay procedures. As expected, the minimum and maximum will vary with different plants and with different antagonists.

Application can be made from solution in a suitable solvent, such as dimethyl sulfoxide. Use can also be made of water as a carrier, especially in emulsified form for commercial application. The treating composition can be used postemergence, as by surface spraying onto the plants, or the antagonist can be supplied with irrigation water to be taken up by the roots of the plant. Application can be made in concentrations within the range of 0.1 to 1000 μg and preferably 10 to 100 μg per liter. Lesser concentrations give little, if any, noticeable anticytokinin effect while dosages of more than 1000 μg per liter in many cases may be undesirable from the standpoint of approaching the lethal dosage.

We claim:
1. A compound having the general formula

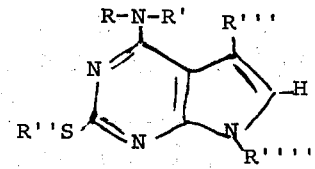

in which R and R' are selected from the group consisting of hydrogen, branched and linear chain C$_1$ - C$_{10}$alkyl, C$_2$ - C$_{10}$ alkenyl, and C$_3$ - C$_{10}$ cycloalkyl, benzyl, phenyl, naphthyl, pyrimidyl, pyridyl and pyrrole, and hydroxy, chloro and bromo substituents of said group, but in which no more than one of the groups R and R' is hydrogen, R" is a group as defined for R and R' and R''' and R'''' are groups selected from the group consisting of hydrogen and a group as defined for R and R'.

2. A compound as claimed in claim 1 in which the compound is a compound having the general formula

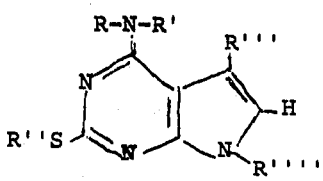

in which R and R' is selected from the group consisting of hydrogen, alkyl and alkenyl each having from 4 to 7 carbon atoms, R'' is selected from the group consisting of $C_1 - C_{10}$ alkyl and $C_2 - C_{10}$ alkenyl, cycloalkyl having from 3 to 10 carbon atoms, benzyl, phenyl, naphthyl, pyrimidyl, pyridyl and pyrrole, and hydroxyl, chloro and bromo substituents of the aforesaid R, R' and R'' groups, but in which no more than one of the groups R and R' is hydrogen, R''' and R'''' are selected from the group consisting of hydrogen and a group as defined for R and R'.

3. A compound as claimed in claim 1 in which the compound is 4-amino-2-alkylthiopyrrolo[2,3-d]-pyrimidine, in which the alkyl has from 1 to 5 carbon atoms, and hydroxy and chloro and bromo derivatives thereof.

4. A compound as claimed in claim 1 in which the compound is 4-amino-2-methylthiopyrrolo[2,3-d]-pyrimidine.

5. A compound as claimed in claim 1 which is 4-cyclopentylamino-2-methylthiopyrrolo[2,3-d]pyrimidine.

6. A compound as claimed in claim 1 which is 4-n-hexylamino-2-methylthiopyrrolo[2,3-d]pyrimidine.

7. A compound as claimed in claim 1 which is 4-n-pentylamino-2-methylthiopyrrolo[2,3-d]pyrimidine.

8. A compound as claimed in claim 1 which is 4-isopentylamino-2-methylthiopyrrolo[2,3-d]pyrimidine.

9. A compound as claimed in claim 1 which is 4-isopentenylamino-2-methylthiopyrrolo[2,3-d]pyrimidine.

10. A compound as claimed in claim 1 which is 4-cyclohexylamino-2-methylthiopyrrolo[2,3-d]pyrimidine.

* * * * *